US009333180B2

(12) United States Patent
Saulnier et al.

(10) Patent No.: US 9,333,180 B2
(45) Date of Patent: *May 10, 2016

(54) NANOCAPSULES WITH A LIQUID LIPID CORE CHARGED WITH WATER-SOLUBLE OR WATER-DISPERSIBLE ACTIVE AGENTS

(75) Inventors: Patrick Saulnier, Marigne (FR); Jean-Pierre Benoit, Angers (FR); Nicolas Anton, Strasbourg (FR)

(73) Assignees: UNIVERSITE D'ANGERS, Angers (FR); INSERM TRANSFERT, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/663,937

(22) PCT Filed: Jun. 11, 2008

(86) PCT No.: PCT/FR2008/051042
§ 371 (c)(1),
(2), (4) Date: Apr. 8, 2010

(87) PCT Pub. No.: WO2009/001019
PCT Pub. Date: Dec. 31, 2008

(65) Prior Publication Data
US 2010/0266676 A1    Oct. 21, 2010

(30) Foreign Application Priority Data
Jun. 11, 2007 (FR) ..................... 07 55652

(51) Int. Cl.
*A61K 9/16* (2006.01)
*A61K 9/50* (2006.01)
*A61K 9/51* (2006.01)
*A61K 9/107* (2006.01)

(52) U.S. Cl.
CPC ............. *A61K 9/5123* (2013.01); *A61K 9/1075* (2013.01)

(58) Field of Classification Search
CPC ...... A61K 9/51; A61K 9/1075; A61K 9/5192; A61K 9/5146; A61K 9/5138; A61K 9/5176
USPC ........................................ 424/489, 490, 488
See application file for complete search history.

(56) References Cited

U.S. PATENT DOCUMENTS

| 5,961,970 A * | 10/1999 | Lowell et al. ................ 424/93.1 |
| 8,057,823 B2 * | 11/2011 | Heurtault et al. ............. 424/498 |
| 9,005,666 B2 * | 4/2015 | Saulnier et al. .............. 424/490 |
| 2003/0152635 A1 * | 8/2003 | Heurtault et al. ............. 424/490 |
| 2004/0076683 A1 | 4/2004 | Hoarau et al. |

FOREIGN PATENT DOCUMENTS

| EP | 1 265 698 | 12/2002 |
| EP | 1 955 695 A1 | 8/2008 |
| EP | 1955695 A1 * | 8/2008 |
| FR | 2 805 761 | 9/2001 |
| FR | 2 840 532 A1 | 12/2003 |

OTHER PUBLICATIONS

Kōzō Shinoda, et al., "The Stability of O/W Type Emulsions as Functions of Temperature and the HLB of Emulsifiers: The Emulsification by PIT-method", Journal of Colloid and Interface Science, vol. 30, No. 2. Jun. 1969, pp. 258-263.
U.S. Appl. No. 12/663,960, filed Dec. 10, 2009, Saulnier, et al.
U.S. Appl. No. 13/139,401, filed Jun. 13, 2011, Benoit, et al.
U.S. Appl. No. 13/260,168, filed Sep. 23, 2011, Benoit, et al.

* cited by examiner

*Primary Examiner* — Michael G Hartley
*Assistant Examiner* — Micah-Paul Young
(74) *Attorney, Agent, or Firm* — Oblon, McClelland, Maier & Neustadt, L.L.P.

(57) ABSTRACT

The invention relates to nanocapsules with a liquid lipidic core and a solid lipidic shell, the lipidic core being loaded with at least one water-soluble or water-dispersible ingredient, said ingredient being present in the form of a reverse micellar system.

20 Claims, No Drawings

NANOCAPSULES WITH A LIQUID LIPID CORE CHARGED WITH WATER-SOLUBLE OR WATER-DISPERSIBLE ACTIVE AGENTS

The present invention is directed toward proposing nanocapsules with a liquid lipid core charged with active agents in this core with at least one water-soluble or water-dispersible active agent.

Nanovesicular systems, of nanocapsule or nanodroplet type whose size ranges from 50 to 500 nanometers and which are formed from a liquid or solid core surrounded by a hydrophobic outer membrane, are already known. The constituents of their membrane may be synthetic, for example of polymeric, protein or lipid nature like liposomes. For example, liposomes that have a lamellar structure formed from a stack of lipid layers separated from each other by aqueous compartments always have an aqueous core.

These nanometric structures have also already been proposed for the purposes of encapsulating active agents either in their aqueous core when the active agent is water-soluble or water-dispersible, or in their lipid layer when the active agent is liposoluble or lipodispersible.

For example, U.S. Pat. No. 5,961,970 proposes, as active agent vehicles, oil-in-water emulsions at the submicron scale, i.e. miniemulsions whose droplets have a hydrophobic core of lipid nature and are surface-stabilized with amphiphilic and/or nonionic surfactants like surfactants of phospholipid type. These droplets are thus maintained in suspension in an aqueous phase. This type of submicron emulsion is obtained from a basic emulsion by subjecting it to several successive homogenization cycles at high shear.

U.S. Pat. No. 5,576,016 describes macroemulsions whose droplets are formed from a solid lipid core and which are stabilized with a phospholipid envelope. This phospholipid envelope has a lamellar structure formed from one or more layers of phospholipid molecules like liposomes. A highly hydrophobic active agent may be charged into the nucleus, and a water-soluble active agent may, on the other hand, be incorporated into the aqueous compartments present in the phospholipid envelope.

Moreover, the inventors have also described in patent EP 1 265 698, as vehicles for liposoluble or lipodispersible active agents, nanocapsules with a liquid core and a solid shell of lipid nature, and novel technology for gaining access thereto. More specifically, these nanocapsules are obtained from a microemulsion, this microemulsion being prepared via the technique of phase inversion via a thermal effect (PIT emulsion).

The principle of phase inversion temperature (PIT) emulsification is well known to those skilled in the art; it was described in 1968 by K. Shinoda (J. Chem. Soc. Jpn, 1968, 89, 435). It was shown that this emulsification technique makes it possible to obtain fine stable emulsions (K. Shinoda and H. Saito, J. Colloid Interface Sci., 1969, 30, 258).

The principle of this technique is as follows: an emulsion, for example a W/O emulsion, is prepared at a temperature that must be higher than the phase inversion temperature of the system, i.e. the temperature at which the equilibrium between the hydrophilic and lipophilic properties of the surfactant system used is reached. At high temperature, i.e. above the phase inversion temperature (>PIT), the emulsion is of water-in-oil type, and, during its cooling, this emulsion becomes inverted at the phase inversion temperature, to become an emulsion of oil-in-water type, and does so by proceeding beforehand through a microemulsion state. This technique makes it possible especially to gain access to a mean size of the globules constituting the oily phase ranging from 0.1 to 4 μm (100 to 4000 nm).

However, the nanocapsules thus obtained are proposed therein merely for the purposes of encapsulating, in their oily core, lipophilic or lipodispersible active agents. Now, for obvious reasons, it would be advantageous also to exploit these nanocapsules for the encapsulation of water-soluble or water-dispersible active agents.

For the purposes of the present invention, the water-dispersible active agent is advantageously a nonlipophilic active agent.

The present invention is directed, specifically, toward proposing a solution for achieving this type of encapsulation.

More specifically, according to a first of its aspects, the present invention is directed toward nanocapsules with a liquid lipid core and a solid lipid shell, charged in the lipid core with at least one water-soluble or water-dispersible active agent, said active agent being incorporated therein in the form of an inverse micellar system.

According to another of its aspects, the present invention relates to a process that is useful for preparing nanocapsules with a liquid lipid core and a solid lipid shell, charged in their lipid core with at least one water-soluble or water-dispersible active agent, said process comprising at least the steps consisting in:

having an oil-in-water emulsion, containing at least one water-soluble or water-dispersible active agent in the form of an inverse micellar system and at least one surfactant system containing at least one hydrophilic, nonionic heat-sensitive surfactant and, where appropriate, a lipophilic surfactant, increasing its temperature up to a temperature $T_2$ above its phase inversion temperature (PIT) to obtain a water-in-oil emulsion, followed by reducing the temperature to a temperature $T_1$, $T_1 < PIT < T_2$ to again obtain an oil-in-water emulsion, performing one or more temperature cycles around the phase inversion zone between $T_1$ and $T_2$, and stabilizing said system at a temperature in or close to the phase inversion zone to form the expected microemulsion, and chill-hardening said microemulsion so as to obtain nanocapsules formed from a lipid core that is liquid at room temperature coated with a lipid shell that is solid at room temperature and comprising said active agent in the form of an inverse micellar system.

The present invention results more particularly from the observation by the inventors that, contrary to all expectation, an oil-in-water emulsion containing at least one water-soluble or water-dispersible active agent in the form of an inverse micellar system proves to be capable of forming, when at least one temperature-mediated phase inversion operation is imposed thereon, a microemulsion whose chill-hardening leads to the formation of nanocapsules containing in their lipid core micelles of water-soluble or water-dispersible active agents. Surprisingly, performing all of the steps necessary to obtain the expected nanocapsules does not affect the stability of the inverse micellar system of the water-soluble or water-dispersible active agent.

Active Agent

For the purposes of the invention, the expression "inverse micellar system of water-soluble or water-dispersible active agent" denotes an architecture in which the water-soluble or water-dispersible active agents are stabilized in an oily phase via the surfactant molecules or the surfactant system forming the micellar system containing the active agent.

For the purposes of the present invention, the water-dispersible active agent is advantageously a nonlipophilic active agent.

Inverse micellar systems are well known to those skilled in the art and are especially exploited for performing selective extractions of proteins or enzymes of interest.

For obvious reasons, the choice of the surfactant system used to form the inverse micellar system is to be made taking into account the solubility of the surfactant(s) of which it is formed, in the oily phase of the oil-in-water emulsion in which the active agent is precisely intended to be formulated. This selection clearly falls within the competence of a person skilled in the art.

Advantageously, the surfactants that are used for producing these inverse micelles and that are suitable for use in the invention have an HLB value of less than 10 and in particular less than or equal to 6. They may belong, without preference, to the families of ionic, nonionic or amphoteric surfactants.

These surfactants may be used in an active agent(s)/surfactant(s) weight ratio ranging from 0.01 to 0.3 and in particular from 0.05 to 0.1.

Advantageously, these surfactants may be associated with co-surfactants, for instance phospholipids. In this respect, phosphatidylcholines (lecithin) are particularly advantageous.

Other phospholipids suitable for use in the invention may be phosphatidylglycerol, phosphatidylinositol, phosphatidylserine, phosphatidic acid or phosphatidylethanolamine.

The inverse micellar system containing the water-soluble or water-dispersible active agent to be encapsulated is prepared prior to being placed in contact with the emulsion so as to stabilize the inverse micelles in the oil.

This oily micellar suspension is then either incorporated at the start of the formulation before the thermal cycle(s), or else added once the system is in its microemulsion form, i.e. in the phase inversion zone of the emulsified system.

For example, they may be prepared as follows:

A hydrophilic active agent, for instance sodium fluorescein crystals, is incorporated with heating at 50° C. and with stirring into an oily phase, for example Lubrafac containing inverse micelles of a surfactant such as Span 80® (10% mass/mass).

As non-limiting illustrations of water-soluble or water-dispersible active agents that may be encapsulated according to the invention, mention may be made especially of 5-fluorouracil, gemcitabine, doxorubicin and low molecular weight heparins.

Besides this water-soluble or water-dispersible active agent encapsulated in their lipid core, the nanocapsules may obviously contain other water-soluble active agents adsorbed in their shell or other liposoluble active agents encapsulated in their lipid core.

For the purposes of the invention, the term "adsorbed" means that the active agent is incorporated into the shell. This absorption phenomenon should be distinguished from simple covalent bonding established between a function present on said active agent and a function present at the surface of the shell of the nanocapsules.

The active agent may especially be a pharmaceutically active or cosmetically active compound or an agent that is active in the plant protection or food sector.

According to one preferred embodiment, this active agent is a pharmaceutically active principle.

In general, the nanocapsules of the invention are more particularly suitable for the administration of the following active principles: anti-infectious agents, including antifungal agents, antibiotics, anticancer agents, immunosuppressants, active principles intended for the central nervous system which must cross the blood-brain barrier, such as antiparkinsonian agents, analgesics and, more generally, active principles for treating neurodegenerative diseases.

Such an active agent may also be of protein or peptide nature. It may also be a nucleic acid such as a DNA plasmid or interference RNA.

The active agent may also be a radiopharmaceutical agent. It may also be a gas or a fluid that can be converted into a gas.

Emulsion and Microemulsion

Firstly, it is important to note that a microemulsion is different than a miniemulsion and than a macroemulsion especially as illustrated in U.S. Pat. Nos. 5,961,971 and 5,576,016. Specifically, a microemulsion corresponds to bi-continuous structuring of the material in the form of micellar structures swollen with oil or water. These micellar structures are highly mutually interlinked, and thus constitute a homogeneous, cohesive, stabilized three-dimensional network. It is therefore not possible to distinguish a dispersed phase from a continuous phase. This microemulsion is in thermodynamic equilibrium, and can therefore exist only under very specific temperature, pressure and composition conditions.

The starting emulsion intended to form the microemulsion may comprise at least one oily fatty phase, one aqueous phase and one surfactant system comprising at least one heat-sensitive, hydrophilic and nonionic surfactant and, where appropriate, according to one preferred embodiment, a lipophilic surfactant.

a—Oily Fatty Phase

The oily fatty phase is formed from at least one fatty substance that is liquid or semiliquid at room temperature, and in particular from at least one triglyceride or fatty acid ester, or a mixture thereof.

The fatty acid ester may be chosen more particularly from $C_8$ to $C_{18}$ and especially $C_8$ to $C_{12}$ fatty acid esters and especially ethyl palmitate, ethyl oleate, ethyl myristate, isopropyl myristate and octyldodecyl myristate, and mixtures thereof.

The triglycerides used may be synthetic triglycerides or triglycerides of natural origin. The natural sources may include animal fats or plant oils, for example soybean oils or sources of long-chain triglycerides (LCT).

Other triglycerides of interest are composed mainly from medium-length fatty acids, also known as medium-chain triglycerides (MCT). A medium-chain triglyceride (MCT) oil is a triglyceride in which the hydrocarbon chain contains from 8 to 12 carbon atoms.

Such MCT oils are commercially available.

As examples of these MCT oils, mention may be made of the TCR products (commercial name from the Société Industrielle des Oléagineux, France, for a triglyceride mixture in which about 95% of the fatty acid chains contain 8 or 10 carbon atoms) and Myglyol® 812 (triglyceride sold by the company Dynamit Nobel, Sweden, for a mixture of caprylic and capric acid glyceride triesters).

The fatty acid units of these triglycerides may be unsaturated, monounsaturated or polyunsaturated. Mixtures of triglycerides containing variable fatty acid units are also acceptable.

It should be noted that the higher the HLB value of the liquid or semiliquid fatty substance, the higher the phase inversion temperature. On the other hand, the HLB value of the fatty substance does not appear to have an influence on the size of the nanocapsules.

Thus, when the size of the end groups of the triglycerides increases, their HLB value decreases and the phase inversion temperature decreases.

The HLB value, or hydrophilic-lipophilic balance, is defined by C. Larpent in Traité K.342 of the Editions Techniques de l'Ingénieur.

The triglyceride sold under the name Labrafac WL 1349® is most particularly suitable for use in the invention.

b—Surfactant System

This surfactant system comprises at least one heat-sensitive, hydrophilic, nonionic surfactant, which may be combined with a lipophilic surfactant.

According to one preferred embodiment, the surfactant system used in the claimed process is formed only from heat-sensitive, hydrophilic, nonionic surfactant(s).

The hydrophilic surfactant is more particularly chosen from emulsifying surfactants of the oil-in-water type usually used that have an HLB value ranging from 8 to 18. These emulsifiers, by virtue of their amphiphilic structure, position themselves at the oily phase/aqueous phase interface and thus stabilize the droplets of dispersed oils.

The surfactant system used in the microemulsion may comprise one or more surfactants whose solubility in the oil increases as the temperature increases. The HLB of these surfactants may range from 8 to 18 and preferably from 10 to 16, and these surfactants may be chosen from ethoxylated fatty alcohols, ethoxylated fatty acids, partial glycerides of ethoxylated fatty acids and polyethoxylated fatty acid triglycerides, and mixtures thereof.

Examples of ethoxylated fatty alcohols that may be mentioned include adducts of ethylene oxide with lauryl alcohol, especially those comprising from 9 to 50 oxyethylene groups (Laureth-9 to Laureth-50 in CTFA names); adducts of ethylene oxide with behenyl alcohol, especially those comprising from 9 to 50 oxyethylene groups (Beheneth-9 to Beheneth-50 in CTFA names); adducts of ethylene oxide with cetostearyl alcohol (mixture of cetyl alcohol and stearyl alcohol), especially those comprising from 9 to 30 oxyethylene groups (Ceteareth-9 to Ceteareth-30 in CTFA names); adducts of ethylene oxide with cetyl alcohol, especially those comprising from 9 to 30 oxyethylene groups (Ceteth-9 to Ceteth-30 in CTFA names); adducts of ethylene oxide with stearyl alcohol, especially those comprising from 9 to 30 oxyethylene groups (Steareth-9 to Ceteareth-30 in CTFA names); adducts of ethylene oxide with isostearyl alcohol, especially those comprising from 9 to 50 oxyethylene groups (Isosteareth-9 to Isosteareth-50 in CTFA names); and mixtures thereof.

Examples of ethoxylated fatty acids that may be mentioned include the adducts of ethylene oxide with lauric, palmitic, stearic or behenic acid, and mixtures thereof, especially those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

Mixtures of these oxyethylenated derivatives of fatty alcohols and of fatty acids may also be used.

These surfactants may also be either natural compounds such as echolate phospholipids or synthetic compounds such as polysorbates, which are polyethoxylated fatty acid esters of sorbitol (Tween®), polyethylene glycol esters of a fatty acid originating, for example, from castor oil (Cremophor®), polyethoxylated fatty acids, for example of stearic acid (Simulsol M-53®), polyoxyethylenated fatty alcohol ethers (Brij®), polyoxyethylenated nonphenyl ethers (Triton N®) and polyoxyethylenated hydroxyphenyl ethers (Triton X®).

It may more particularly be a polyethylene glycol 2-hydroxystearate and especially the product sold under the name Solutol® HS15 by the company BASF (Germany).

As stated previously, the surfactant system adopted according to the invention advantageously comprises, besides the heat-sensitive, hydrophilic nonionic surfactant, at least one lipophilic surfactant.

The lipophilic surfactant is more particularly based on phospholipids that are advantageous with regard to their biocompatible nature.

Among the phospholipids, phosphatidylcholines (lecithin) are particularly advantageous.

Other phospholipids may be phosphatidylglycerol, phosphatidylinositol, phosphatidylserine, phosphatidic acid and phosphatidylethanolamine.

The phospholipid derivatives may be isolated from natural sources or prepared via synthesis.

As commercial products derived from phospholipids, mention may be made more particularly of:

Epicuron 120® (Lukas Meyer, Germany), which is a mixture of about 70% phosphatidylcholine, 12% phosphatidylethanolamine and about 15% other phospholipids;

Ovotine 160® (Lukas Meyer, Germany), which is a mixture comprising about 60% phosphatidylcholine, 18% and phosphatidylethanolamine and 12% other phospholipids;

a mixture of purified phospholipids such as the products Lipoid E75 or Lipoid E80 (Lipoid®, Germany), which is a mixture of phospholipids comprising about 80% by weight of phosphatidylcholine, 8% by weight of phosphatidylethanolamine, 3.6% by weight of nonpolar lipids and 2% of sphingomyelin.

According to one preferred embodiment, the lipophilic surfactant is a lecithin whose proportion of phosphatidylcholine ranges from 40% to 80% by weight.

Lipoid S75-3 (Lipoid® GmbH, Germany) is most particularly suitable as a source of phosphatidylcholine. It is soybean lecithin. This product contains about 69% phosphatidylcholine and 9% and phosphatidylethanolamine. This constituent is the only constituent that is solid at 37° C. and at room temperature in the formulation.

Polyglyceryl-6 dioleate (Plurol®) may also be used.

The liquid fatty substance/lipid surfactant(s) ratio may range from 1 to 15, preferably from 1.5 to 13 and more preferentially from 3 to 8.

It should be noted that the particle size decreases when the proportion of hydrophilic surfactant increases and when the proportion of surfactants (hydrophilic and, where appropriate, lipophilic) increases. Specifically, the surfactant entrains a decrease in the interface tension and thus stabilization of the system, which promotes the production of small particles.

Moreover, the particle size increases when the proportion of oil increases.

For its part, the aqueous phase of the microemulsion may also advantageously contain 1% to 4% of a salt, especially a mineral salt, for instance sodium chloride. Specifically, modification of the salt concentration results in shifting of the phase inversion zone. Thus, the higher the salt concentration, the lower the phase inversion temperature. This phenomenon proves to be most particularly advantageous for the encapsulation of hydrophobic heat-sensitive active principles.

According to one particular embodiment, the microemulsion advantageously contains from 1% to 3% of lipophilic surfactant(s), from 5% to 15% of hydrophilic surfactant(s), from 5% to 15% of an oily phase and from 64% to 89% of an aqueous phase (the percentages are expressed on a weight basis relative to the total weight of the microemulsion).

According to one embodiment, a microemulsion of the invention may be formed from at least one fatty acid triglyceride and a polyethylene glycol 2-hydroxystearate derivative, and, where appropriate, a lecithin.

In one preferred embodiment, the fatty phase is a fatty acid triglyceride, the lipophilic surfactant is a lecithin and the hydrophilic surfactant is a polyethylene glycol 2-hydroxystearate derivative and especially Solutol® HS15.

As stated previously, the emulsion under consideration according to the invention is converted into a microemulsion according to the phase inversion technique, in particular via a change in temperature.

This temperature-mediated phase inversion is advantageously brought about by imposing on the emulsion at least one cycle of temperature rise and fall.

Repetition of the temperature cycles is advantageous in several respects. Thus, it has been found that during the temperature cycles the shell of the nanoparticles that form after chill-hardening advantageously becomes thicker and thus more stable.

Furthermore, it should be noted that the temperature of the phase inversion zone has a tendency to decrease gradually in the course of the imposed temperature cycles. This phenomenon is precisely advantageous when the active agent that it is desired to encapsulate or adsorb is a temperature-sensitive active agent. Under such conditions, introduction of the active agent at the time of a temperature-compatible cycle is favored.

More specifically, before the chill-hardening intended to form the nanocapsules charged with at least one hydrophilic active agent, the emulsion under consideration according to the invention is subjected at least to the steps consisting in:
  increasing its temperature up to a temperature $T_2$ above the phase inversion temperature (PIT) to obtain a water-in-oil emulsion, followed by decreasing the temperature to a temperature $T_1$, $T_1 < PIT < T_2$ to again obtain an oil-in-water emulsion,
    where appropriate, performing one or more temperature cycles around the phase inversion zone between $T_1$ and $T_2$ and
    stabilizing said system at a temperature that is in or close to the phase inversion zone to form the expected microemulsion.

Thus, one or more temperature cycles may advantageously be performed around the phase inversion zone between $T_1$ and $T_2$, until a translucent suspension is observed, which corresponds to the formation of a microemulsion. The system is then stabilized at a temperature that corresponds to the structuring of the system as the expected microemulsion.

More specifically, the phase inversion between the oil/water emulsion and the water/oil emulsion is reflected by a decrease in conductivity when the temperature increases, until it becomes cancelled out.

Thus, $T_1$ is a temperature at which the conductivity is at least equal to 90-95% of the conductivity measured at 20° C. and $T_2$ is the temperature at which the conductivity cancels out and the water-in-oil emulsion forms. The mean temperature of the phase inversion zone corresponds to the phase inversion temperature (PIT).

In the zone for formation of a microemulsion (translucent mixture), the hydrophilic and hydrophobic interactions are equilibrated since the surfactant system has a tendency to form both direct micelles and inverse micelles. By heating beyond this zone, formation of a W/O emulsion takes place (white opaque mixture), since the surfactant promotes the formation of a water-in-oil emulsion. Next, during cooling below the phase inversion zone, the emulsion becomes an O/W emulsion.

The number of cycles applied to the microemulsion depends on the amount of energy required to form the nanocapsules.

This technology is more particularly described in patent EP 1 265 698, the content of which is incorporated into the present patent application.

Thus, all the constituents intended to form the microemulsion are weighed out in a container. The mixture is homogenized, for example using a Rayneri blender at 350 rpm, and heated by gradually raising the temperature using a water bath up to a temperature greater than or equal to the phase inversion temperature $T_2$, i.e. until a transparent or translucent phase is obtained (microemulsion or lamellar phase zone), and then until a more viscous white phase is obtained, which indicates that the inverse emulsion (W/O) has been obtained. Heating is then stopped and stirring is maintained until the emulsion has cooled to room temperature, passing through the phase inversion temperature $T_1$, i.e. the temperature at which the expected microemulsion forms. When the temperature has fallen below the phase inversion temperature ($T_1$), this stable microemulsion is obtained.

The microemulsion that has been formed is subsequently subjected to chill-hardening according to the invention.

This step for forming the nanocapsules according to the invention consists of sudden cooling (or chill-hardening) of the microemulsion at a temperature suitable for solidification of the interfacial films composing the microemulsion, advantageously to a temperature very much below $T_1$, with magnetic stirring.

For example, chill-hardening of said microemulsion charged at least with said active agent may be performed at a temperature at least 30° C. below the PIT at the time of the chill-hardening.

This chill-hardening may be performed by diluting the medium 3- to 10-fold with deionized water at 2° C.±1° C. thrown into the fine microemulsion. The nanocapsules obtained are kept stirring for 5 minutes.

The organization of the system in the form of nanocapsules after chill-hardening is reflected visually by a change in the appearance of the initial system, which changes from opaque-white to translucent-white with a Tyndall effect (bluish tints). This change takes place at a temperature below the PIT. This temperature is generally between 6 and 15° C. below the PIT.

After the process according to the invention, nanocapsules charged in their lipid core with at least one water-soluble active agent are obtained.

For the purposes of the invention, the term "nanocapsules" should be distinguished from nanospheres. The term "nanocapsules" means particles formed from a core that is liquid or semiliquid at room temperature, coated with a film that is solid at room temperature, as opposed to nanospheres, which are matrix particles, i.e. all of the mass is solid. Thus, when nanospheres contain a pharmaceutically active principle, it is finely divided in the solid matrix.

Advantageously, the nanocapsules obtained according to the invention have a mean size of less than 150 nm, preferably less than 100 nm and more preferably less than 50 nm. These sizes may be determined by photon correlation spectroscopy, scanning electron microscopy, or transmission electron microscopy in cryoscopic mode.

The thickness of the solid film or shell is advantageously between 2 and 10 nm. It is also about a tenth of the diameter of the particles. This thickness may be calculated via the mass balance, or visualized by negative-shadow transmission electron microscopy or alternatively by transmission electron microscopy in cryoscopic mode.

Given their size, the nanocapsules of the invention are colloidal lipid particles.

The polydispersity index of the nanocapsules of the invention is advantageously between 5% and 15%. This index is determined on the size histogram obtained via the photon correlation spectroscopy method.

The nanocapsules are each formed from an essentially lipid core that is liquid or semiliquid at room temperature, coated with an essentially lipid shell that is solid at room temperature.

For the purposes of the invention, the term "essentially lipid" means that the core and the shell forming the nanocapsules according to the invention are formed from more than 50% by weight, in particular more than 75% by weight, especially more than 80% by weight, or even more than 90% and more particularly more than 95% of their respective weight, or even totally, from one or more lipid (hydrophobic) compounds.

According to one embodiment, a nanocapsule according to the invention may comprise a shell formed from at least one lipophilic surfactant that is solid at room temperature.

The nanocapsules in accordance with the invention are particularly advantageous as vehicles for formulating active agents. For example, these nanocapsules may be useful for manufacturing plant-protection or pharmaceutical compositions.

The present invention is also directed toward compositions containing nanocapsules in accordance with the invention.

For the purposes of the invention, the term "room temperature" denotes a temperature ranging from 18 to 25° C.

The present invention is illustrated by the examples that follow, which are given as nonlimiting illustrations of the field of the invention.

EXAMPLE 1

Preparation of Nanocapsules Whose Lipid Core is Charged with a Water-Soluble Active Agent 5 g of an emulsion containing 75 mg of Lipoid S75-3®, 504 mg of lipophilic Labrafac WL 1349®, 504 mg of Solutol HS®, 15.383 g of water and 88 mg of sodium chloride are prepared.

In parallel, sodium fluorescein crystals (10 mg) are incorporated with heating at 50° C. into the Labrafac (3 g) containing inverse micelles of Span 80 (0.6 g) (20% mass/mass).

After homogenization of this micellar suspension, 0.25 ml thereof is introduced into the preceding emulsion.

The whole is placed under magnetic stirring. Heat is applied until a temperature of 85° C. is reached. With continued magnetic stirring, the system is allowed to cool to a temperature of 60° C. These heating cycles (between 85° C. and 60° C.) are performed three times so as to obtain microemulsions that are more and more structured. The system is then maintained in its microemulsion form by stabilizing it at a temperature that is within (or close to) the phase inversion zone, in the present case 65° C.

The nanocapsules are finished by chill-hardening in cold water (5° C.). The nanocapsules are separated from the medium by centrifugation.

The invention claimed is:

1. A nanocapsule having a liquid lipid core and a solid lipid shell, charged in the lipid core with at least one water-soluble or water-dispersible active agent, said active agent being present therein in the form of an inverse micellar system.

2. The nanocapsule according to claim 1, in which the inverse micellar system comprises a surfactant system formed from at least one surfactant having an HLB of less than 10.

3. The nanocapsule according to claim 2, in which the surfactant is used in an active agent(s)/surfactant(s) weight ratio ranging from 0.01 to 0.3.

4. The nanocapsule according to claim 1, in which the core is formed from at least one liquid or semiliquid fatty substance.

5. The nanocapsule according to claim 4, in which the core comprises at least one triglyceride, one fatty acid ester, or a mixture thereof.

6. The nanocapsule according to claim 4, in which the core is formed from at least one lipophilic surfactant that is solid at room temperature.

7. The nanocapsule according to claim 6, in which the lipophilic surfactant is based on phospholipid, and optionally is a lecithin whose proportion of phosphatidylcholine is between 40% and 80% by weight.

8. The nanocapsule according to claim 6, in which the liquid fatty substance/lipophilic surfactant ratio ranges from 1 to 15.

9. The nanocapsule according to claim 1, which has a mean size of less than 150 nm.

10. The nanocapsule according to claim 1, which has a solid shell thickness ranging from 2 to 10 nm.

11. The nanocapsule according to claim 1, in which the active agent is a pharmaceutically active or cosmetically active compound or an agent that is active in the plant-protection or food sector.

12. A process for preparing nanocapsules having a liquid lipid core and a solid lipid shell, charged in their lipid core with at least one hydrophilic active agent, said process comprising:
preparing an inverse micellar system by incorporating a hydrophilic active agent into an oily phase with stirring and heating, wherein the inverse micellar system comprises an oily dispersion of inverse micelles incorporating the hydrophilic active agent,
preparing an oil-in-water emulsion, comprising at least one hydrophilic active agent in said inverse micellar system and at least one surfactant system comprising at least one hydrophilic, nonionic, heat-sensitive surfactant,
increasing the temperature of the emulsion up to a temperature $T_2$ above its phase inversion temperature (PIT) to obtain a water-in-oil emulsion, followed by reducing the temperature to a temperature $T_1$, where $T_1<PIT<T_2$, to again obtain an oil-in-water emulsion,
optionally, performing one or more temperature cycles around the phase inversion zone between $T_1$ and $T_2$,
stabilizing said system at a temperature in or close to the phase inversion zone to form the expected microemulsion, and
chill-hardening said microemulsion in order to obtain nanocapsules formed from a lipid core that is liquid at room temperature coated with a lipid shell that is solid at room temperature and comprising in the liquid lipid core said active agent in the form of an inverse micellar system.

13. The process according to claim 12, in which the hydrophilic surfactant has an HLB ranging from 8 to 18.

14. The process according to claim 12, in which the hydrophilic surfactant is chosen from ethoxylated fatty alcohols, ethoxylated fatty acids, partial glycerides of ethoxylated fatty acids and polyethoxylated fatty acid triglycerides, and mixtures thereof.

15. The process according to claim 12, in which the oily fatty phase comprises at least one liquid fatty compound chosen from at least one triglyceride, one fatty acid ester, or a mixture thereof.

16. The process according to claim 12, in which the surfactant system also comprises at least one lipophilic surfactant.

17. The process according to claim 12, in which the lipophilic surfactant is solid at room temperature.

18. The process according to claim 12, in which the inverse micellar system comprises a surfactant system formed from at least one surfactant having an HLB of less than 10.

19. The process according to claim 12, in which the microemulsion is formed from at least one fatty acid triglyceride and one polyethylene glycol 2-hydroxystearate derivative, and, optionally, a lecithin.

20. A composition comprising nanocapsules having a liquid lipid core and a solid lipid shell, charged in the liquid core with at least one water-soluble or water-dispersible active agent, said active agent being present therein in the form of an inverse micellar system.

\* \* \* \* \*